(12) United States Patent
Furst et al.

(10) Patent No.: US 7,945,409 B2
(45) Date of Patent: May 17, 2011

(54) METHOD FOR VERIFYING POSITION ON AN ANGIOPLASTY BALLOON

(75) Inventors: Joseph G. Furst, Lyndhurst, OH (US); William Brodbeck, South Euclid, OH (US)

(73) Assignee: ICON Interventional Systems, Inc., Atlanta, GA (US)

( * ) Notice: Subject to any disclaimer, the term of this patent is extended or adjusted under 35 U.S.C. 154(b) by 2008 days.

(21) Appl. No.: 10/900,765

(22) Filed: Jul. 28, 2004

(65) Prior Publication Data

US 2005/0159802 A1 Jul. 21, 2005

Related U.S. Application Data

(60) Provisional application No. 60/536,777, filed on Jan. 15, 2004.

(51) Int. Cl.
G06F 19/00 (2006.01)
G06F 17/40 (2006.01)

(52) U.S. Cl. .......... 702/81; 73/865.8; 700/109; 702/187

(58) Field of Classification Search ................ 73/432.1, 73/865.8; 623/1.1, 1.11, 1.12, 66.1; 700/90, 700/95, 108, 109, 110, 117; 702/1, 33, 34, 702/35, 81, 82, 84, 127, 182, 187
See application file for complete search history.

(56) References Cited

U.S. PATENT DOCUMENTS

| | | | | |
|---|---|---|---|---|
| 2,721,701 A | * | 10/1955 | Hardesty et al. | 377/16 |
| 2,767,914 A | * | 10/1956 | Merrill et al. | 702/82 |
| 2,883,255 A | * | 4/1959 | Anderson | 346/34 |
| 4,303,984 A | * | 12/1981 | Houvig | 702/104 |
| 4,418,392 A | * | 11/1983 | Hata | 702/91 |
| 4,868,476 A | * | 9/1989 | Respaut | 318/632 |
| 5,089,979 A | * | 2/1992 | McEachern et al. | 702/91 |
| 5,423,334 A | * | 6/1995 | Jordan | 128/899 |
| 5,672,169 A | | 9/1997 | Verbeek | |
| 5,836,952 A | | 11/1998 | Davis et al. | |
| 5,860,966 A | | 1/1999 | Tower | |
| 5,893,852 A | | 4/1999 | Morales | |
| 5,893,867 A | | 4/1999 | Bagaoisan et al. | |
| 5,911,752 A | | 6/1999 | Dustrude et al. | |
| 5,931,851 A | | 8/1999 | Morales | |
| 5,951,540 A | | 9/1999 | Verbeek | |
| 5,992,000 A | | 11/1999 | Humphrey et al. | |
| 6,009,614 A | | 1/2000 | Morales | |
| 6,018,857 A | | 2/2000 | Duffy et al. | |
| 6,024,737 A | | 2/2000 | Morales | |
| 6,033,380 A | | 3/2000 | Butaric et al. | |
| 6,051,002 A | | 4/2000 | Morales | |
| 6,063,092 A | | 5/2000 | Shin | |
| 6,063,102 A | | 5/2000 | Morales | |
| 6,206,916 B1 | | 3/2001 | Furst | |
| 6,327,501 B1 | * | 12/2001 | Levine et al. | 607/27 |
| 6,360,577 B2 | | 3/2002 | Austin | |

(Continued)

FOREIGN PATENT DOCUMENTS

WO WO 03/037398 5/2003

Primary Examiner — Edward R Cosimano
(74) Attorney, Agent, or Firm — Fay Sharpe LLP; Brian E. Turung

(57) ABSTRACT

A monitoring system and data archive system for a stent crimping process. The information concerning the crimped stent is used in deciding whether the stent is acceptable for insertion into the body cavity of a human or animal.

21 Claims, 2 Drawing Sheets

U.S. PATENT DOCUMENTS

| | | |
|---|---|---|
| 6,385,593 B2 * | 5/2002 | Linberg .......................... 705/28 |
| 6,436,133 B1 | 8/2002 | Furst et al. |
| 6,442,432 B2 * | 8/2002 | Lee ................................ 607/59 |
| 6,629,350 B2 | 10/2003 | Motsenbocker |
| 6,651,478 B1 | 11/2003 | Kokish |
| 6,689,123 B2 | 2/2004 | Pinchasik |
| 6,726,713 B2 | 4/2004 | Schaldach et al. |
| 6,763,132 B2 * | 7/2004 | Freifeld ........................ 382/152 |
| 6,988,881 B2 * | 1/2006 | Motsenbocker et al. ..... 425/392 |
| 7,240,833 B2 * | 7/2007 | Zarembo ........................ 235/385 |
| 7,333,013 B2 * | 2/2008 | Berger ..................... 340/539.12 |
| 7,757,543 B2 * | 7/2010 | Freeman et al. .............. 73/25.01 |
| 2001/0001890 A1 * | 5/2001 | Austin ............................ 29/282 |
| 2002/0099438 A1 | 7/2002 | Furst |
| 2002/0163104 A1 * | 11/2002 | Motsenbocker et al. ...... 264/320 |
| 2003/0040790 A1 | 2/2003 | Furst |
| 2003/0223632 A1 * | 12/2003 | Freifeld ........................ 382/152 |
| 2005/0247319 A1 * | 11/2005 | Berger ............................ 128/898 |
| 2005/0258242 A1 * | 11/2005 | Zarembo ....................... 235/385 |
| 2007/0187240 A1 * | 8/2007 | Araya et al. ................... 204/424 |
| 2008/0021307 A1 * | 1/2008 | Freeman et al. .............. 600/424 |

* cited by examiner

METHOD FOR VERIFYING POSITION ON AN ANGIOPLASTY BALLOON

The present invention claims priority on U.S. Provisional Patent Application Ser. No. 60/536,777 filed Jan. 15, 2004 entitled "Method for Verifying Drug Coated Stent Apposition on an Angioplasty Balloon Before and After Crimping" which is incorporated by reference herein.

The present invention relates to intraluminal grafts and particularly to coated or non-coated intraluminal grafts that are modified in shape such as, but not limited to, crimping.

INCORPORATION BY REFERENCE

United States Patent Publication No. 2003/0040790 entitled Stent Coating and 2002/0099438 entitled Irradiated Stent Coating, and U.S. Pat. No. 6,436,133 entitled Expandable Graft and U.S. Pat. No. 6,206,916 entitled Coated Intraluminal Graft, and PCT Publication No. WO 03/037398 entitled Improved Stent Coating are incorporated herein by reference. U.S. Pat. Nos. 5,860,966; 5,893,852; 5,893,867; 5,911,752; 5,931,851; 5,951,540; 5,992,000; 6,009,614; 6,024,737; 6,033,380; 6,051,002; 6,063,092; 6,063,102; and 6,360,577, and United States Patent Publication No. 2002/0163104 entitled Balloon Folding Technology are also incorporated herein by reference. U.S. Pat. Nos. 5,672,169; 5,836,952; 5,931,851; 5,951,540; 5,992,000; 6,018,857; 6,024,737; 6,051,002; 6,063,092; 6,063,102; 6,009,614; 6,629,350; 6,651,478; 6,689,123 and 6,726,713 are further incorporated herein by reference.

BACKGROUND OF THE INVENTION

Drug coated stents or stents that do not have any drug coating (bare metal) are commonly mounted on an angioplasty balloon prior to being inserted into a body cavity. The angioplasty balloon is used to expand the stent and set the stent in position in a body cavity once the stent is positioned in a desired location in the body cavity.

Typically the stent is mounted on the angioplasty balloon by first positioning the angioplasty balloon between the proximal and distal marker bands on the stent so that the angioplasty balloon is properly centered in the interior cavity of the stent. The sent is then crimped to maintain the angioplasty balloon in the stent so that angioplasty balloon is maintained in the proper position in the stent as the stent is positioned in a desired location of a body cavity. The stent may also be crimped to form the body of the stent into a particular shape. Once the stent is properly positioned in the body cavity, the angioplasty balloon is expanded thereby causing the stent to expand. After the stent has been expanded, the angioplasty balloon is deflated and removed from the stent and body cavity.

The positioning of the angioplasty balloon in the stent and the proper crimping of the stent are important to achieve the proper expansion of the stent and the desired performance of the stent. If the angioplasty balloon is not properly positioned in the stent, the stent may not properly expand in the body cavity, thereby increasing the chances of stent failure. If the stent is not properly crimped to maintain the angioplasty balloon in a proper position in the stent as the stent is inserted in a body cavity, the angioplasty balloon may become repositioned in the stent after the stent is crimped and/or as the stent is being inserted in a body cavity. The repositioning of the angioplasty balloon may result in the stent being improperly expanded in the body cavity, thereby increasing the chances of stent failure. If the stent is to be crimped to form the body of the stent in a particular shape, the shape of the body of the stent must be correct after crimping to achieve the desired shape after expansion of the stent; otherwise, an improperly shaped expanded stent may increase the occurrence of stent failure. In addition, the crimping process must be properly performed so as to not damage the stent and/or any coating on the stent. If the stent is damaged, the stent may not properly expand in the body cavity, may break during expansion, may be structurally weakened, and/or the shape of the crimped stent may be adversely altered and interfere with the proper insertion of the stent into a body cavity. A damaged and/or adversely shaped stent thereby increases the chances of stent failure. Many stents are now coated with materials to reduce the rejection of the stent, to reduce in-stent restenosis, to treat a medical condition, and/or for many other or additional reasons. If, during the crimping process, the drug and/or medicine coating on the stent is damaged, the proper amount of drug and/or medication may not be delivered to a body site, thereby possibly increasing the occurrence of stent failure and/or the improper treatment of a body site with the drug and/or medication. Stents are also coated with drugs and/or medications that are time released. The damage to the coating can adversely affect the time during which the drug and/or medication is released, thus increasing the occurrence of stent failure and/or the improper treatment of a body site with the drug and/or medication. If a coating on the stent is used to reduce rejection of the stent, the damage to such coating can result in increased occurrences of stent failure.

Although the proper mounting of the angioplasty balloon in the stent is very important to the success of the stent being inserted in a body cavity, the present day practice is to merely visually inspect the stent after the angioplasty balloon has been inserted in the stent to determine if the angioplasty balloon has been properly positioned in the stent and that the stent has been properly crimped. Several automated devices have been developed to crimp the stent in order to increase the uniformity of the final crimped stents and to reduce the occurrence of improperly crimped stents. These crimped stents that are formed by such automated devices are typically visually inspected to ensure that the crimped stent has not been significantly damaged during the crimping process. Thereafter, the stent is packaged for use. Detailed information concerning the crimped stent is not available or is difficult to obtain by a physician prior to the stent being inserted into a human or animal.

In view of the present state of the art, there is needed a method and apparatus for inspecting a stent to determine if an angioplasty balloon has been properly inserted in a stent, to determine that the stent has been properly crimped, and/or to determine that the stent and/or coating on the stent has not be damaged. There is also a need in the art for a method and apparatus for tracking the information pertaining to the stent and the crimping of the stent so that better informed decisions can be made to use a particular stent to thereby increase the success rate of an inserted stent.

SUMMARY OF THE INVENTION

The present invention is directed to an improved apparatus and method of inspecting an intraluminal graft, and particularly to the inspection of an intraluminal graft prior to, during and/or after the crimping of the intraluminal graft to determine if the intraluminal graft has been properly modified in shape, whether an angioplasty balloon has been properly inserted in the intraluminal graft, to determine whether the intraluminal graft as been damaged, and/or determine if a coating, if used, on the intraluminal graft has been damaged.

The present invention is specifically directed to intraluminal grafts in the form of stents (whether self-expanding, balloon expandable or a combination of self-expanding and balloon expandable) that are used in a body cavity such as, but not limited to, blood vessels; however, the invention has broader applications and is intended to cover stents for use in any type of body passageway, and is also intended to include intraluminal grafts other than stents (e.g., stent-grafts, grafts, vena cava filters and other endoluminal prostheses whether self-expanding, balloon expandable or a combination of self-expanding and balloon expandable, etc.).

In one aspect of the present invention, there is provided one or more devices to obtain information about a stent. Such information about the stent can include, but is not limited to, size of the stent, composition of the stent, shape of the stent prior to crimping of the stent, shape of the stent during crimping of the stent, shape of the stent after crimping of the stent, position of angioplasty balloon in the stent prior to crimping the stent, position of an angioplasty balloon in the stent during the crimping of the stent, position of an angioplasty balloon in the stent after the crimping of the stent, the condition of the angioplasty balloon prior to crimping of the stent, the condition of the angioplasty balloon in the stent during crimping of the stent, condition of an angioplasty balloon in the stent after crimping of the stent, type of one or more coatings on the stent, location of one or more coatings on the stent, status of one or more coatings on the stent prior to crimping the stent, status of one or more coatings on the stent during crimping of the stent, status of one or more coatings on the stent after crimping of the stent, structural integrity of the stent prior to crimping of the stent, structural integrity of the stent during crimping of the stent, structural integrity of the stent after crimping of the stent, and/or the like. The one or more devices that are used to obtain information about the stent include, but are not limited to, a camera, a video recorder, a microscope (e.g., optical, electron, etc.), visual or electromagnetic wave imaging device (e.g., infrared device, ultraviolet device, x-ray device, CAT scan device, CT device, PET device, SPECT device, MRI device, ultrasound device, etc.), EDS analyzing device, ICP analyzing device, etc. One or more of these devices can be used to obtain information about the stent prior to crimping the stent, during the crimping of the stent, and/or after the crimping of the stent. When the one or more devices are used to monitor one or more parameters of the stent prior to, during, and/or after the crimping process, the one or more devices can be positioned near the stent to monitor one or more steps of the crimping process. Such information can include, but is not limited to, parameters of the crimping process, location(s) of the crimp, identification of any coating anomalies, identification of any stent anomalies, identification of any damage to the stent or any improper crimping of the stent, identification of any damage to coating of the stent, type of the stent, date/time of crimping, machine/procedure used to crimp, personnel in charge of crimping, crimping facility, type of coating on the stent, positioning of angioplasty balloon in the stent before, during and/or after crimping of the stent, etc. The information relating to the stent and the crimping of the stent can be used to monitor, document and/or facilitate in ensuring the quality control of the stent and/or to review information about the stent prior to the stent being used. Such quality control can result in an increased success in medical procedures involving stents.

In another and/or alternative aspect of the invention, the information obtained on the stent is recorded so that such information can be more easily and readily retrieved. The stent can be encoded with one or more types of information and/or one or more types of information can be stored on one or more forms of retrievable storage. In one embodiment of the invention, the stent is encoded with one or more types of information. The coding of the stent can be physically placed on the stent, can be included on the packaging and/or label associated with the stent, and/or be a separate device that is packaged with and/or otherwise associated with the stent. The coding on the stent itself can include, but is not limited to, magnetic coding (e.g., imprinting the stent with magnetic pulses, modified frequency modulation, etc.), visual coding (e.g., colored markings, bar codes, etc.) and/or physical coding (e.g., indents, ribs, etc.). When the encoding is an electrically or electronically readable device or component other than the stent itself, such device or component can include, but is not limited to, RFID (radio frequency identification) cards or tags, bar code labels or tabs, ROM, IC (integrated circuit) plates or boards, Touch Memory buttons, and the like. Touch Memory is a registered trademark of Dallas Semiconductor Corporation of Dallas, Tex. The encoded information can additionally or alternatively be retained on other types of media such as, but not limited to, printed or developed material (e.g., photographs, informational printout, printed tags, printed labels, etc.), and/or storage media (e.g., hard disk, DVD, memory stick, CD, film, floppy disk, magnetic tape, zip disk, etc.). As can be appreciated, one or more types of information relating to the stent can be stored on a personal computer or personal network, the internet, palm device, etc. The encoded information pertaining to the stent can include a variety of different types of information such as, but not limited to, generic or fixed information such as the product name and/or trademark associated with the stent and/or stent coating, the package type, and/or the like; information about the stent prior to, during, and/or after the crimping of the stent as set forth above. The encoded information can be updated so as to include information such as, but not limited to, the shipping and/or inventory information associated with the stent, when a stent has been used, etc. With respect to inventory information, the encoded information can provide a user or facility with information on how many and/or what types of stents have been used, how long in storage a stent has been maintained, etc. to notify the user and/or facility that additional stents need to be ordered and/or expired stents need to be disposed of. With respect to shipping information, the encoded information can be used to track the shipment of the stent from the manufacturer or storage facility to another location. With respect to information about when the stent was used, such information can include, but is not limited to, date/time the stent was used, the name of the patient in which the stent was used, the facility that was used to insert the stent into a patient, the physician and/or personnel associated with the medical procedure for inserting the stent into a patient, medical information relating to the surgical procedure for inserting the stent into a patient, information used that is associated with the selection of the stent for use in the medical procedure, etc. The information relating to the stent can be manually and/or automatically entered and/or stored. The information could be allowed to be modified by authorized personnel. The various types of information relating to the stent can be electronically and/or visually reviewed and/or analyzed to obtain information about the stent prior to, during and/or after the stent has been inserted into a patient. The various types of information can also and/or alternatively archived and/or saved for later review and/or analysis.

In still another and/or alternative aspect of the present invention, the one or more devices that are used to obtain information about the stent are included on and/or are positioned adjacent to a crimping device. The crimping device can be a manual crimping device, semi-automatic crimping device or automatic crimping device. The one or more devices that are used to obtain information about the stent can record and/or generate information on the stent and/or be included with the stent after the stent has been crimped. In one embodiment of the invention, the stent is crimped by an automated crimping machine and information associated with the crimping process and/or resulting stent is recorded on archiveable media. The information that is recorded is then associated with the stent. One non-limiting example is that a bar code is associated with the crimped stent and placed on the stent and/or packaging of the stent. This bar code can include information on the stent and/or provide an identification code that can be used to obtain information on the stent from an archiveable information storage system (e.g., computer database, file system, microfiche, etc.). The archiveable information storage system is designed to enable a physician and/or other authorized personnel to more readily obtain information about a particular stent and to use such information to assist in a decision as to whether to use the stent in a particular medical procedure. In another and/or alternative embodiment of the invention, the information obtained on the stent during the crimping process can be used to identify improperly crimped stents. The data obtained on the stent can be manually and/or automatically analyzed to identify crimped stents that do not meet quality parameters and/or are improperly crimped.

It is an object of the present invention to provide information on intraluminal grafts.

Another and/or alternative embodiment of the invention is to provide information on intraluminal grafts to determine the quality of the intraluminal grafts.

Still another and/or alternative object of the present invention is to provide information pertaining to characteristics of the intraluminal graft.

Yet another and/or alternative object of the present invention is to provide an intraluminal graft having information encoded on the intraluminal graft, on packaging associated with the intraluminal graft, and/or visually marked on the intraluminal graft.

Still yet another and/or alternative object of the present invention is to provide an intraluminal graft with information that can be used to track the shipping, manufacture and/or use of the intraluminal graft.

A further and/or alternative object of the present invention is to monitor and/or record information about the manufacture, the coating, and/or the crimping of an intraluminal graft and to record such information for retrieval and review.

Still a further and/or alternative object of the present invention is to facilitate in ensuring the use of high quality intraluminal grafts for insertion in a human or animal.

Yet a further and/or alternative object of the present invention is to reduce the failure rate of intraluminal grafts.

Still yet a further and/or alternative object of the present invention is to increase the ease of obtaining information of a crimped stent.

Another and/or alternative object of the present invention is to provide information on a crimped stent to facilitate in determining whether such stent is acceptable to be inserted into a body cavity.

These and other objects and advantages will become apparent from the discussion of the distinction between the invention and the prior art and when considering the preferred embodiment as shown in the accompanying drawings.

BRIEF DESCRIPTION OF THE DRAWINGS

The foregoing objects, and others, will in part be obvious and in part pointed out more fully hereinafter in conjunction with the written description of preferred embodiments of the invention illustrated in the accompanying drawings in which.

DETAILED DESCRIPTION OF AN EMBODIMENT

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the body cavity such as, but not limited to, a blood vessel. In its expanded configuration, the stent supports and reinforces the body cavity walls while maintaining the body cavity in an open, unobstructed condition. Expandable stents are well known and widely available in a variety of designs and configurations. Expandable stents are commonly crimped to their reduced diameter about the delivery catheter, then maneuvered to the deployment site and expanded to the body cavity diameter by fluid inflation of a balloon that is typically positioned between the stent and the delivery catheter. The present invention is particularly directed to the crimping of expandable stents that are expanded by angioplasty balloons; however, the invention can be applied to self-expanding stents.

In advancing an expandable balloon through a body vessel to the deployment site, the stent must be able to securely maintain its axial position on the delivery catheter, without translocating proximally or distally, and especially without becoming separated from the catheter. Stents that are not properly secured or retained to the catheter may slip and either be lost or be deployed in the wrong location or partially deployed. The stent must be crimped in such a way as to minimize or altogether prevent distortion of the stent and thereby prevent abrasion and/or reduce trauma of the body cavity walls. The stent must also be crimped in such a way as to avoid damaging the angioplasty balloon, when used.

Crimping of a stent that has been done by hand often results in the application of undesired and/or uneven forces to the stent. Such a stent must either be discarded or re-crimped. Stents which have been crimped multiple times can suffer from fatigue and may be scored or otherwise marked which can cause thrombosis. A poorly crimped stent can also damage the underlying angioplasty balloon, when such balloon is used. Automated crimping devices have been developed to reduce the inconsistencies associated with hand crimping. The present invention is directed to a method, system and device for obtaining information concerning the crimped stent that can be used for quality control of the stent and/or to later provide information about the stent and/or one or more processes associated with the crimping of the stent. The invention is particularly applicable for use with automatic or semi-automatic crimping machines; however, the invention can be used with manual crimping devices.

Figure 1:
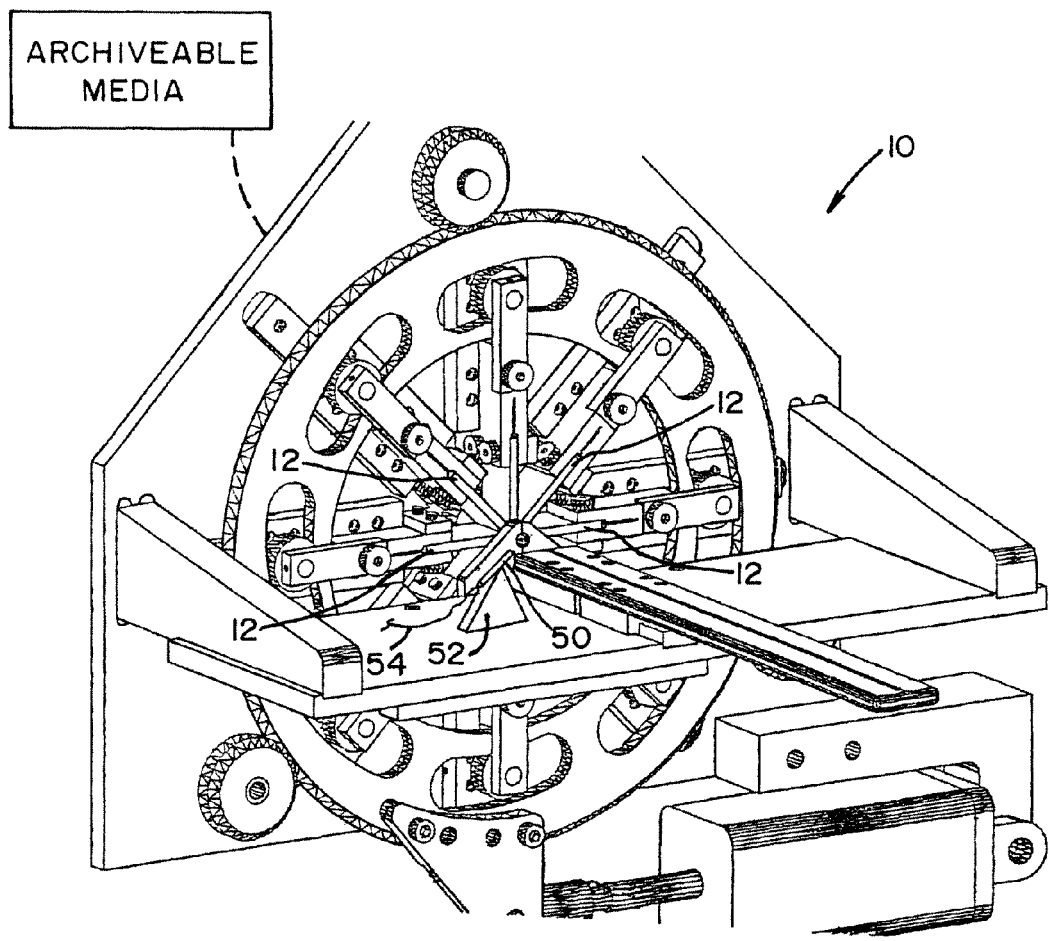
FIG. 1 illustrates one type of crimping machine that can be used to crimp a stent.

Referring now in greater detail to the drawings, wherein the showings are for the purpose of illustrating a preferred embodiment of the invention only and not for the purpose of limiting the invention, FIG. 1 illustrates one type of automated crimping device that can be used in the present invention. A detailed description of this crimping device and the various modifications or associated with this crimping device are disclosed in United States Patent Publication No. 2001/0001890, which is incorporated herein by reference. As such, a detailed description of the crimping device will not be repeated herein. As can be appreciated, other types of crimping machines can be used in association with the present invention.

Figure 2:
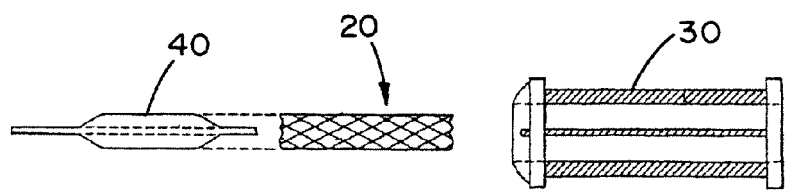
FIG. 2 illustrates the insertion of an angioplasty balloon into the body of a stent prior to the stent being crimped; and, FIG. 3 is a flow chart illustrating one embodiment of the invention.

The crimping device 10 illustrated in FIG. 1 is designed to shape and/or reduce the size of stent 20 illustrated in FIG. 2. The crimping machine typically includes one or more dies 30 illustrated in FIG. 2. The stent is crimped by the use of at least three coupled movable blades disposed about the die 30. Each blade is in communication with an actuation device 12 which is capable of moving the blade to alter the size of the aperture of the die.

In use, stent 20 is inserted into the die and the blades are moved into contact with the stent to reduce the diameter of the stent and/or shape the stent. The stent can be crimped with or with a balloon catheter 40 inserted in the body of the stent. A typical crimping sequence includes the following steps:
1) presize stent using any suitable means (optional);
2) load stent onto balloon and catheter (optional);
3) position stent into stent crimper; and
4) crimp the stent.

The stent can be rotated and/or slid in die 30, as necessary, to obtain the desired final crimped configuration of the stent. As thus far described, the typical techniques for crimping a stent have been set forth.

Referring again to FIG. 1, the crimping device includes a monitoring device 50. As shown in FIG. 1, the monitoring device 50 is mounted on a stand 52 to enable the monitoring device to be positioned closely adjacent to the outlet of die 30. Monitoring device 50 is illustrated in FIG. 1 as being a camera that is designed to take images of the stent after it has been crimped. As can be appreciated, the monitoring device can be designed to take images of the stent prior to and/or during the crimping of the stent. It can be appreciated that more than one monitoring device and/or more than one type of monitoring device can be used to obtain information about the stent prior to, during, and/or after the crimping process. It can also be appreciated that one or more monitoring devices can be located in the die of the crimping machine. An electric cord 54 is shown to be attached to the end of the camera and is designed to transmit data from the camera to a storage device. As can be appreciated, the information from the camera can be alternatively or additionally transmitted wirelessly to a storage media.

The resolution of the camera can be selected to obtain general information about the stent or selected to obtain detailed information about one or more regions of the stent. As can be appreciated, the resolution of the camera can be adjusted to obtain multiple resolutioned images of the stent to provide both general and detailed information on the stent prior to, during, and/or after the crimping process. In one configuration of the invention, the monitoring device is designed to obtain both general and specific images of the stent. The general images can be used to view the stent as a whole or larger regions of the stent to determine that the stent has obtained the desired shape after being crimped, the angioplasty balloon, if used, has been properly positioned in the stent after being crimped, and/or the stent has not been damaged during the crimping process. The more detailed information obtained by the monitoring device can include information such as whether cracks or other signs of fatigue have occurred in specific regions of the stent after crimping, whether a coating on the stent, if used, has been damaged during the crimping process, whether the angioplasty balloon, if used, has been damaged during the crimping process, whether any of the ends of the stent are impermissibly sharp and/or include jagged edges, etc. The imaging of the stent is taken at least after the stent has been crimped; however, additional imaging information can be obtained prior to and/or during the crimping of the stent to compare this information to the information relating to the stent after crimping and/or to provide a more complete history of the stent during the crimping process.

The information obtained by the monitoring device 50 relating to the stent is transferred to an archiveable media. The archiveable media is typically an electronic medium, such as a data storage disk, which can be used to both store the information concerning the stent which was obtained by the monitoring device, and to enable relatively quick access to such information when needed. As can be appreciated, the information obtained on the stent can be saved on more than one type of archiveable media. For instance, the information obtained about the stent can be printed out and stored in a file system and also be stored in an electronic storage base. As can be appreciated, many other and/or additional arrangements can be used to store the information concerning the stent on an archiveable media.

The information obtained by the monitoring device used to monitor the crimped stent can consist of the complete record for the stent or be combined with other information concerning the stent. Such other information could include the material composition of the stent, the manufacturing location of the stent, the time of manufacture of the stent, the process for manufacturing the stent, the personnel involved in manufacturing the stent, the types of coatings, if any, which were applied to the stent, the procedures associated with applying the coatings to the stent, the acceptable life of the coatings applied to the stent, the personnel and/or process involved in applying the coatings to the stent, the size of the stent, the configuration of the stent, the locations where the stent has been transported or stored, the location in a body cavity in which the stent is designed to be used, the name of the patient in which the stent is to be inserted, the location in the patient in which the stent is to be inserted, the procedure by which the stent is inserted into a patient, the time and/or facility where the stent was inserted into a patient, the personnel involved in the insertion of the stent into a patient, the time and/or date the stent was reviewed for quality control purposes, the time, date, and/or name of any individual who has reviewed the stent or any information concerning the stent, and/or any other type of information which is associated with the stent. As such, a complete history of the stent could be maintained on an archiveable media for review by a physician or other authorized personnel. This information could be used to approve the use of the stent in a patient, reject the use of the stent for use in a particular patient, cause the stent to be further inspected to ensure that the stent is appropriate for use in a patient, provide data for various types of studies that are used to monitor the performance of certain types of stents, etc.

The information obtained by monitoring device 50 can also or alternatively be used for quality control for the stent after the stent has been crimped and/or at other or additional phases of the manufacture and/or use of the stent. If the crimping of the stent is being performed by a semi-automatic or automatic crimping machine, the information obtained by the monitoring device can be used by the crimping machine to automatically reject stents that do not fall within certain predefined parameters and/or to flag certain stents which are suspected as not falling within all the predefined parameters for the crimped stent. These flagged stents could then be manually inspected to ensure that the requirements are met for the particular crimped stent. The information obtained by monitoring device 50 could also be used to manually review the crimped stents that are formed by a manual crimping process, a semi-automatic crimping process and/or an automatic crimping process. The various information and/or images provided by the monitoring device could be immediately displayed to one or more quality control personnel and/or stored in a retrievable storage media for subsequent retrieval by one or more quality review personnel to review the quality of the crimped stent.

After the stent has been crimped, one or more portions of the information concerning the stent are inserted on the stent itself and/or are associated with the labeling and/or packaging for the stent. Information that could be included on the stent includes magnetically imprinting information or an ID code on the stent which could be later retrieved by various electronic devices, imprinting a number sequence, bar code sequence and/or color coding sequence on the stent which would provide information about the stent and/or providing an ID code that could be used to obtain information relating to the stent. The stent may additionally or alternatively include one or more labels which contains information relating to the stent and/or an identification sequence or code that can be used to obtain information about the stent. For instance, the label could include a bar code number sequence and/or a color code sequence that could be read in, scanned in, and/or manually inputted to obtain access to the archiveable information associated with the stent. The packaging for the stent may include printed matter that includes data relating to the stent and/or includes number sequences, bar code sequences, color code sequences, etc. which could be used to obtain access to the archiveable information relating to the stent. The packaging of the stent could also include various types of storage media, such as zip disks, floppy disks, memory sticks, RFID cards or tags, IC plates or boards, Touch Memory buttons, etc. which could be used to store various types of data concerning the stent that could be retrieved by an authorized physician and/or personnel. As can be appreciated, the archival information relating to the stent can be maintained on multiple archiveable media so that if one form of archiveable media is unavailable and/or inaccessible, a secondary source could be accessed. For instance, the packaging for the stent could include a zip disk which includes most, if not all, of the archiveable information relating to the stent. However, if the disk becomes lost, damaged or inaccessible, the archiveable information could also be stored on a network system which could be accessed through an intranet and/or internet so as to enable a physician and/or authorized personnel to access one or more portions of the archiveable information relating to the stent through this secondary archiveable media source. The stent and/or packaging could also include a bar code which could be used to provide an identification and/or access code to access information on an intranet and/or internet system. As can be appreciated, many other and/or alternative arrangements can be used to ensure that the archiveable information relating to the stent can be readily and easily accessed by a physician and/or authorized personnel.

Figure 3:
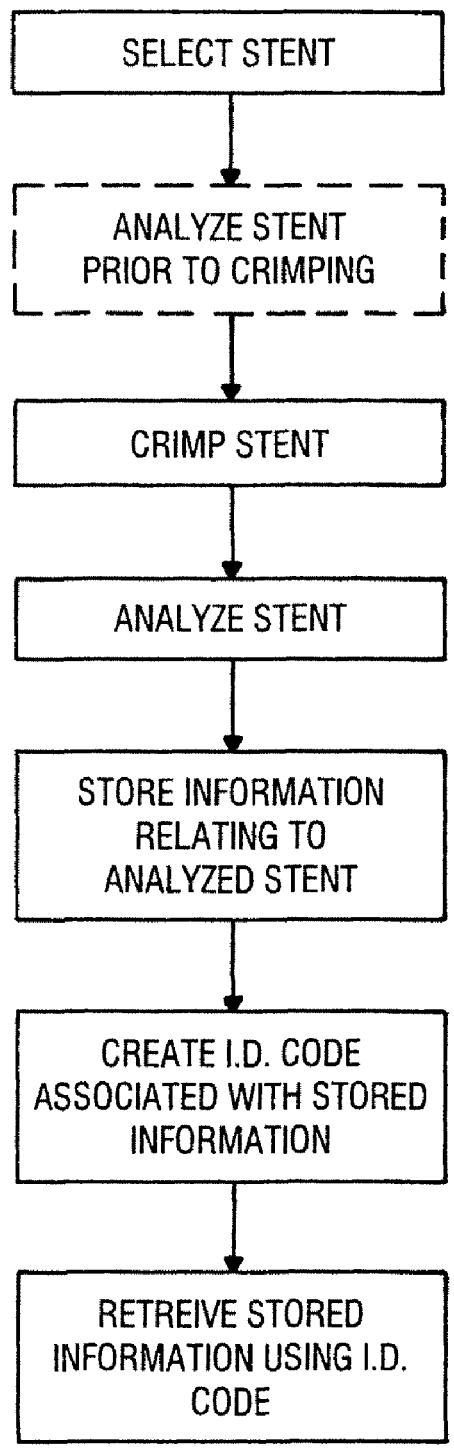

Referring now to FIG. 3, a flow chart is set forth which illustrates one particular embodiment of the invention. As shown in FIG. 3, a particular stent is selected for a crimping process. The criteria for selecting a particular stent is typically based upon the patient, a particular medical procedure, the criteria set forth by the physician that is to use the stent in a particular medical procedure, etc. Once the stent is selected, the stent can be analyzed prior to crimping. This analysis can be manually conducted and/or can be conducted by a monitoring device that records various parameters of the stent prior to the crimping process. This step is an optional process, thus is illustrated in a dashed box. The next step is to crimp the stent by a manual crimping device, a semi-automatic crimping device, or an automatic crimping device. If an angioplasty balloon is to be inserted in the stent, the angioplasty balloon is inserted into the body of the stent prior to the crimping process. During and/or after the crimping of the stent, the stent is analyzed by a monitoring device which is used to store information relating to the crimped stent in an archiveable media. An ID code is created for use in obtaining access to the archived information on the stent. This ID code is typically imprinted on the stent, applied to a label for the stent, and/or included on the packaging or packaging information for the stent. When the archived information relating to the stent needs to be reviewed by a physician and/or authorized personnel, the ID code for the stent can be manually entered, scanned, etc. so as to provide access to archived information that has been electronically saved.

The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention.

We claim:

1. A method of making a record of a stent crimping process comprising:
   a. providing a stent;
   b. crimping the stent;
   c. monitoring said stent at least after the crimping of said stent; and,
   d. recording said monitoring on an archiveable media.

2. The method as defined in claim 1, wherein said step of monitoring includes a monitoring device, said monitoring device includes a camera, a video recorder, a microscope, a visual or electromagnetic wave imaging device, or combinations thereof.

3. The method as defined in claim 2, wherein said archiveable media includes printed or developed material, storage media, or combinations thereof.

4. The method as defined in claim 1, including the step of monitoring and analyzing a condition of said crimped stent.

5. The method as defined in claim 4, wherein said step of monitoring and analyzing includes i) analyzing said archiveable information associated with said crimped stent, and ii) determining whether said crimped stent is acceptable for insertion into a body cavity based on a visual inspection of said crimped stent and a review of said archiveable information.

6. The method as defined in claim 1, wherein said step of monitoring includes monitoring said stent prior to insertion of an angioplasty balloon into said body of said stent, monitoring said stent during insertion of an angioplasty balloon into said body of said stent, monitoring said stent after insertion of an angioplasty balloon into said body of said stent, monitoring said stent prior to crimping said stent, monitoring said stent during said crimping of said stent, monitoring said stent after said crimping of said stent, monitoring the condition of a coating on said stent prior to crimping said stent, monitoring the condition of a coating on said stent during crimping said stent, monitoring the condition of a coating on said stent after crimping said stent, or combinations thereof.

7. The method as defined in claim 6, wherein said step of monitoring includes a monitoring device, said monitoring device includes a camera, a video recorder, a microscope, a visual or electromagnetic wave imaging device, or combinations thereof.

8. The method as defined in claim 7, wherein said archiveable media includes printed or developed material, storage media, or combinations thereof.

9. The method as defined in claim 1, wherein said archiveable media includes printed or developed material, storage media, or combinations thereof.

10. The method as defined in claim 9, wherein said storage media includes said stent, a RFID card or tag, a ROM, an IC plate or board, a Touch Memory button, a hard disk, a DVD, a memory stick, a CD, film, a floppy disk, a magnetic tape, a zip disk, the body of said stent, or combinations thereof.

11. The method as defined in claim 9, wherein said printed material includes a bar code.

12. The method as defined in claim 1, including the step of inserting an angioplasty balloon in a body of the stent and crimping the stent after the angioplasty balloon is at least partially positioned in the body of said stent.

13. The method as defined in claim 12, wherein said step of monitoring includes monitoring said stent prior to insertion of an angioplasty balloon into said body of said stent, monitoring said stent during insertion of an angioplasty balloon into said body of said stent, monitoring said stent after insertion of an angioplasty balloon into said body of said stent, monitoring said stent prior to crimping said stent, monitoring said stent during said crimping of said stent, monitoring said stent after said crimping of said stent, monitoring the condition of a coating on said stent prior to crimping said stent, monitoring the condition of a coating on said stent during crimping said stent, monitoring the condition of a coating on said stent after crimping said stent, or combinations thereof.

14. The method as defined in claim 13, wherein said step of monitoring includes a monitoring device, said monitoring device includes a camera, a video recorder, a microscope, a visual or electromagnetic wave imaging device, or combinations thereof.

15. The method as defined in claim 14, wherein said archiveable media includes printed or developed material, storage media, or combinations thereof.

16. The method as defined in claim 15, wherein said storage media includes said stent, a RFID card or tag, a ROM, an IC plate or board, a Touch Memory button, a hard disk, a DVD, a memory stick, a CD, film, a floppy disk, a magnetic tape, a zip disk, the body of said stent, or combinations thereof.

17. The method as defined in claim 15, including the step of monitoring and analyzing a condition of said crimped stent.

18. The method as defined in claim 17, wherein said step of monitoring and analyzing includes i) analyzing said archiveable information associated with said crimped stent, and ii) determining whether said crimped stent is acceptable for insertion into a body cavity based on a visual inspection of said crimped stent and a review of said archiveable information.

19. The method as defined in claim 15, wherein said printed material includes a bar code.

20. The method as defined in claim 19, including the step of monitoring and analyzing a condition of said crimped stent.

21. The method as defined in claim 20, wherein said step of monitoring and analyzing includes i) analyzing said archiveable information associated with said crimped stent, and ii) determining whether said crimped stent is acceptable for insertion into a body cavity based on a visual inspection of said crimped stent and a review of said archiveable information.

* * * * *